Figure 1:
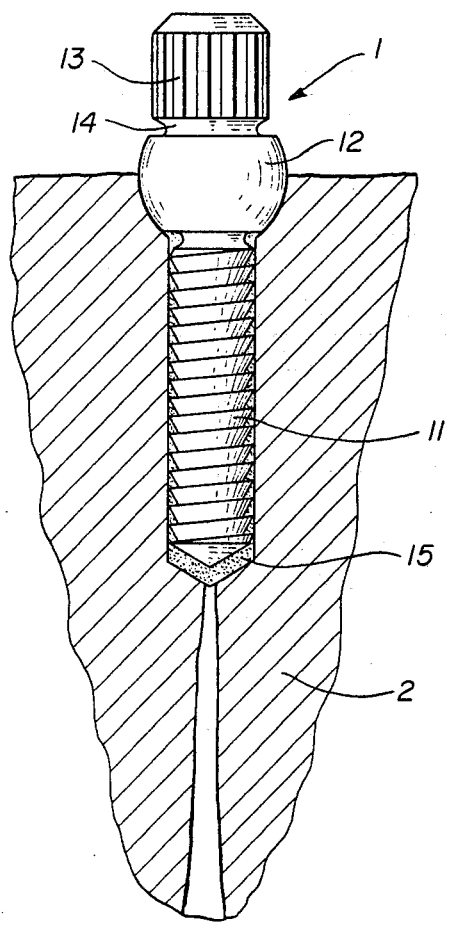

United States Patent [19]

Borle

[11] 4,334,865
[45] Jun. 15, 1982

[54] DENTAL OBTURATION SCREW

[76] Inventor: Jean-Pierre Borle, Rue Camille-Martin No. 20, 1203 Geneve, Switzerland

[21] Appl. No.: 202,434

[22] Filed: Oct. 30, 1980

[30] Foreign Application Priority Data

Nov. 5, 1979 [CH] Switzerland .................. 9901/79

[51] Int. Cl.³ .............................. A61C 5/08
[52] U.S. Cl. ................................. 433/221; 433/174
[58] Field of Search .............. 433/220, 221, 174, 173, 433/175, 180, 201

[56] References Cited

U.S. PATENT DOCUMENTS

| 430,522 | 6/1890 | Genese | 433/221 |
|---|---|---|---|
| 1,285,785 | 11/1918 | McMahon et al. | 433/221 |
| 2,411,758 | 11/1946 | Ruetz | 433/221 |
| 2,655,724 | 10/1953 | Brooks | 433/221 |
| 3,085,334 | 4/1963 | Bischof et al. | 433/180 |
| 3,672,058 | 6/1972 | Nikoghossian | 433/174 |
| 4,185,383 | 1/1980 | Heimke et al. | 433/201 |

FOREIGN PATENT DOCUMENTS

| 464497 | 8/1928 | Fed. Rep. of Germany | 433/220 |
|---|---|---|---|
| 1058354 | 3/1964 | France | 433/220 |

Primary Examiner—Gene Mancene
Assistant Examiner—John J. Wilson
Attorney, Agent, or Firm—Cushman, Darby & Cushman

[57] ABSTRACT

A dental obturation screw is disclosed which comprises a threaded rod and a screw head allowing to actuate the screw and to fasten thereon an articial tooth or tooth part. The screw has a bearing part of convex, axially symmetrical shape which is adapted to rest on a corresponding bearing surface of the part of a natural tooth to be obturated.

5 Claims, 2 Drawing Figures

U.S. Patent Jun. 15, 1982 4,334,865

DENTAL OBTURATION SCREW

The present invention relates to a dental obturation screw having a threaded rod and a screw head, said screw head comprising a crown part allowing to actuate the screw and to fasten thereon an artificial tooth or tooth part.

Dental obturation screws of this type are inserted in the remaining part of a natural tooth and in particular in the root canal thereof, the upper part of said screw being used for supporting an artifical tooth structure. Those screws are therefore subjected to considerable forces during mastication, which is one of the causes of the risk of disintegration of the threaded rod.

It is a main object of the invention to reduce the dangers for the remaining part of a natural tooth during the insertion and during the subsequent use of an obturation screw of the above mentioned type.

In accordance with the invention, a dental obturation screw comprises a bearing part of convex shape symmetrically arranged about the screw axis between the threaded rod and the crown part thereof. The bearing part has preferably the shape of spherical segment and its height between the largest and the smallest diameter thereof is substantially equal or greater than the height of a corresponding recess of same shape in the remaining part of a natural tooth.

The invention also relates to a method of preparing the recess in the natural tooth part by means of a diamond reamer and to the special shape of said diamond reamer. Further objects, features and advantages of the invention will appear more clearly from the following detailed description of an embodiment of the invention presented by way of example. In the accompanying drawing FIG. 1 is an axial sectional view of the remaining part of a natural tooth with an obturation screw according to the invention inserted therein, and FIG. 2 is a side view of a diamond reamer for use in connection with the obturation screw shown in FIG. 1.

Figure 2:
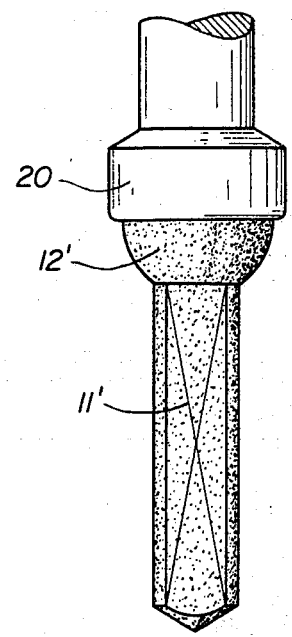

FIG. 1 shows an obturation screw 1 inserted in a part of natural tooth 2 schematically represented in cross section. Screw 1 comprises a cylindrical threaded rod 11 and a screw head including a bearing part 12 and a crown part 13, an intermediate part 14 forming an annular groove therebetween.

The bearing part 12 has preferably the shape of a spherical segment, the greatest diameter of which is substantially greater than the diameter of the threaded rod 11. An annular groove is shown to be formed between the threaded rod 11 and the bearing part 12. The thread is preferably of saw-tooth shape with a top angle of 60° and a small pitch. The screw crown 13 is shown to comprise a milled cylindrical part adapted to allow actuating the screw by means of an appropriate key, for instance a swivelling ball-joint key.

The present obturation screw is preferably used as follows:

In the remaining part of a natural tooth comprising in particular one or more roots of the tooth, a recess is formed the shape of which is substantially the same as the outer shape of the part of the obturation screw which will be lodged in the tooth part. Said recess comprises a cylindrical part of a slightly greater diameter than that of the threaded rod 11 and of a slightly greater length than that of the threaded rod, for example longer by 1 thread pitch. The upper part of said recess is formed by a concave part the depth of which is substantially equal to or slightly less than the height of the bearing part 12 between its sections of greatest and smallest diameter.

The recess in the natural tooth is preferably formed by means of a diamond reamer such as represented in FIG. 2. The shown reamer comprises a first diamond part 11' which is constituted for instance by two diametrically opposite parts of a cylindrical surface connected to each other by two parallel plane surfaces, the tip of part 11' being formed with an angle of about 120°. A upper cutting part 12' has the shape of a spherical segment corresponding to the part 12 in FIG. 1 comprised between the sections of greatest and of smallest diameter thereof. Both parts 11' and 12' are diamond coated and fixed to a support part 20 adapted to be fitted to an appropriate rotatable tool member not represented in FIG. 2. The support part 20 has a greater diameter than the upper section of part 12' thus forming a protective collar which restricts the drilling depth of the reamer.

Dental cement 15 is introduced into the recess formed by the reamer shown in FIG. 2, and the dental screw 1 is inserted by means of a tool adapted on the screw head 13. Due to the fact that rod 11 does not reach the bottom of the recess when the bearing part 12 is fitted in the corresponding recess of the natural tooth, the insertion of the screw practically results in no radial and axial forces on the natural tooth part and the bearing 12 rests closely on the upper concave part of the recess. The mastication forces acting on the artificial tooth structure fixed onto the obturation screw and transmitted to the same are thus distributed over a relatively large surface in the upper part of the remaining part of the natural tooth by the bearing part 12. The convex shape of the bearing part in particular shows an optimal distribution of said forces.

The dental obturation screw according to the invention allows to reduce to a minimum the risks of damaging the roots and the remaining part of a natural tooth as well when inserting the screw as during the subsequent use of the artificial tooth. The present screw is of a simple shape which implies only low manufacturing costs. The functional requirements of this screw are however optimally satisfied. Furthermore, the corresponding recess can be made by a very precise, long lasting tool, the cost of which is also relatively low. The invention therefore provides an advantageous solution from the point of view of manufacturing and offers the best guarantee of success from the prosthetical point of view.

I claim:

1. A dental obturation screw for inserting in the root canal of a natural tooth, said screw having a threaded cylindrical rod and a screw head, said screw head comprising a crown part allowing to actuate the screw and to fasten thereon an artificial tooth part, and comprising a solid uninterrupted bearing part of convex shape symmetrically arranged about the screw axis between said threaded rod and said crown part and having a greatest diameter substantially greater than the diameter of the threaded rod, whereby said bearing part is adapted to rest on a corresponding bearing surface to obturate the root canal of the natural tooth.

2. A dental obturation screw as claimed in claim 1, wherein said bearing part has the shape of a spherical segment.

3. A dental obturation screw as claimed in claim 2, wherein said crown part comprises a milled cylindrical actuating part and a part forming an annular groove between said cylindrical actuating part and said bearing part.

4. A dental obturation screw as claimed in claim 1, wherein said convex shape of said bearing part is in axial direction at least as high as a corresponding recess of same shape in the remaining part of a natural tooth, between the greatest and the smallest diameter thereof.

5. A dental obturation screw as claimed in claim 1, wherein said convex shape of said bearing part has between its greatest and its smallest diameter the same height as a corresponding part of same shape of a diamond reamer, and the length of said threaded rod is less than the length of a corresponding cutting part of said diamond reamer.

* * * * *